United States Patent [19]

Ryder et al.

[11] Patent Number: 4,817,998
[45] Date of Patent: Apr. 4, 1989

[54] INSTRUMENT FOR HANDLING CONTACT LENS DISINFECTING CATALYST

[75] Inventors: Francis E. Ryder, Arab; Rowland W. Kanner, Guntersville, both, Ala.

[73] Assignee: Ryder International Corporation, Arab, Ala.

[21] Appl. No.: 80,780

[22] Filed: Aug. 3, 1987

[51] Int. Cl.⁴ .................... B65D 85/38; A61L 2/18
[52] U.S. Cl. .................... 294/1.1; 294/1.2; 206/5.1; 422/300
[58] Field of Search .......... 294/1.1, 1.2; 206/5.1; 422/300, 301

[56] References Cited

U.S. PATENT DOCUMENTS

| | | | |
|---|---|---|---|
| 3,063,083 | 11/1962 | Obitts | 294/1.2 |
| 3,314,533 | 4/1967 | Kopzle | 206/5.1 |
| 3,770,133 | 11/1973 | Thomas | 206/5 A |
| 4,011,941 | 3/1977 | Parsons | 206/51 |
| 4,396,583 | 8/1981 | LeBoeuf | 422/301 |
| 4,637,919 | 1/1987 | Ryder et al. | 422/300 |
| 4,750,610 | 6/1988 | Ryder | 206/5.1 |

Primary Examiner—James B. Marbert
Attorney, Agent, or Firm—Trexler, Bushnell, Giangiorgi & Blackstone

[57] ABSTRACT

An extractor instrument for removing a catalytic ring, or the like, normally held by friction at the bottom of a container cavity, enabling the container to be fabricated with an integrally closed bottom wall opposite the open upper end of the container. The instrument comprises an elongate gripping member and a cam structure secured to the gripping member adjacent one end. The cam structure includes a foot dimensioned for insertion through a passageway in the catalytic ring after which the foot is engaged in a camming manner against the bottom surface of the ring allowing withdrawal of the foot and the engaged ring from the open end of the container.

17 Claims, 2 Drawing Sheets

INSTRUMENT FOR HANDLING CONTACT LENS DISINFECTING CATALYST

BACKGROUND OF THE INVENTION

This invention relates to instruments for handling small articles, particularly consumable catalyst elements employed in disinfecting contact lenses.

The widely used soft contact lenses generally require disinfecting treatment to prevent eye-damaging growth of microorganisms. In addition to a disinfecting treatment of the lenses using boiling solutions, an alternative disinfecting treatment has been developed in which hydrogen peroxide solution is decomposed to liberate disinfecting oxygen, as described in U.S. Pat. No. 4,011,941. This patent describes a lens storage container in which the hydrogen peroxide decomposition and disinfection treatment are promoted by a layer of catalytic platinum deposited on a molded ring. The catalytic ring is gradually deactivated and periodically replaced. In order to provide acces to the ring for replacement, the ring is held on a removable bottom of the lens container to which it must be secured by a post projecting from the bottom. Accordingly, this arrangement requires that not only the top of the container, but also the bottom of the container be fabricated for disassembly from the container body, increasing the complexity and expense of fabrication.

SUMMARY OF THE INVENTION

In accordance with this invention an extractor instrument is provided for removing a catalytic ring or the like, normally held by friction at the bottom of a container cavity, enabling the container to be fabricated with an integrally closed bottom wall opposite the open upper end of the container. The instrument comprises an elongate gripping member and a cam structure secured to the gripping member adjacent one end. The cam structure includes a foot dimensioned for insertion through a passageway in the catalytic ring after which the foot is engaged in a camming manner against the bottom surface of the ring allowing withdrawal of the foot and the engaged ring from the open end of the container.

In a preferred embodiment, three beveled feet facilitate cammed wedging of the feet between the ring and the bottom wall of the container to lift the ring from the bottom wall upon manually twisting the gripping member. The feet extend generally perpendicular to a cylindrical stem aligned with the elongate dimension of the gripping member. The three feet are spaced in an annular pattern complementary for clearance through the passageway configuration of the ring. At least one of the feet can be provided with a stop blade which prevents excessive rotation of the feet with respect to the ring to prevent their disengagement prior to removal of the ring from the container cavity.

Optionally, the instrument can be provided with structure for inserting the catalytic ring into the container for placement adjacent the bottom wall. The structure for the ring insertion can be provided by a cylindrical pin, formed at the end of the instrument opposite the cam structure, with a diameter dimensioned to project into the passageway of the catalytic ring. A supporting flange is formed adjacently below the pin to support the ring with the pin inserted through the passageway, which allows the inverted container body to be lowered over the ring and instrument until the ring is frictionally fitted against the bottom wall of the container after which the pin and instrument can be withdrawn.

The instrument can be additionally provided with an integral memory device including multiple insignia formed on the gripping member corresponding to a calendar for scheduling and reminding the user to remove and replace the catalytic ring. The gripping member can be fabricated as a generally flat handle within which twelve punch-tabs are formed with respective tab labels on the gripping member corresponding with calendar months. Both surfaces of the gripping handle can be provided with the calendar labels for labeling each tab with two staggered months corresponding to a predetermined sequence for the latest and next scheduled replacement of the catalytic ring.

DETAILED DESCRIPTION OF THE ILLUSTRATED EMBODIMENT.

Figure 1:
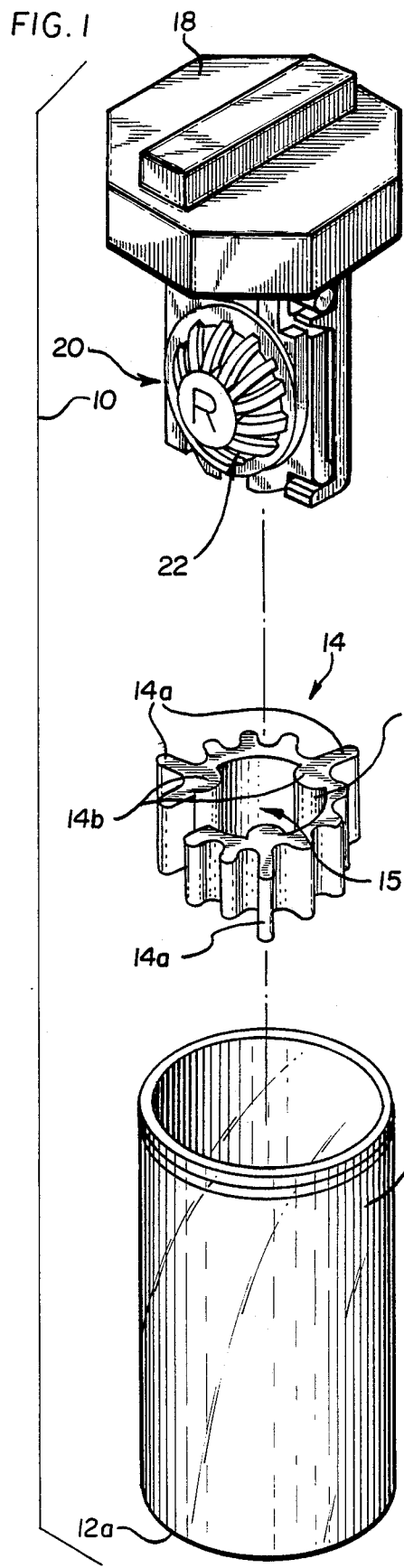
FIG. 1 is an exploded, perspective view of an embodiment of the storage and disinfection lens case and illustrating a replaceable catalytic element which is removable by employing the instrument of the invention in an embodiment shown in FIG. 2.
Figure 2A:
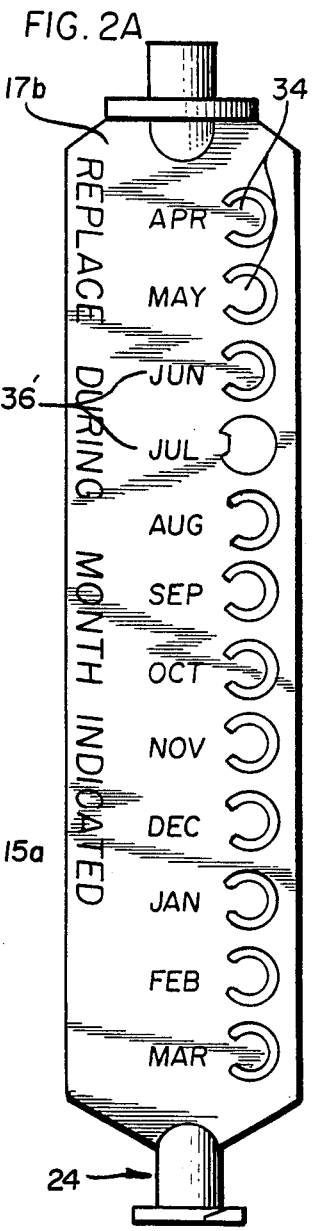
FIGS. 2 and 2a are a front elevation views of front and rear surfaces of an embodiment of the instrument of the invention.
Figure 2:
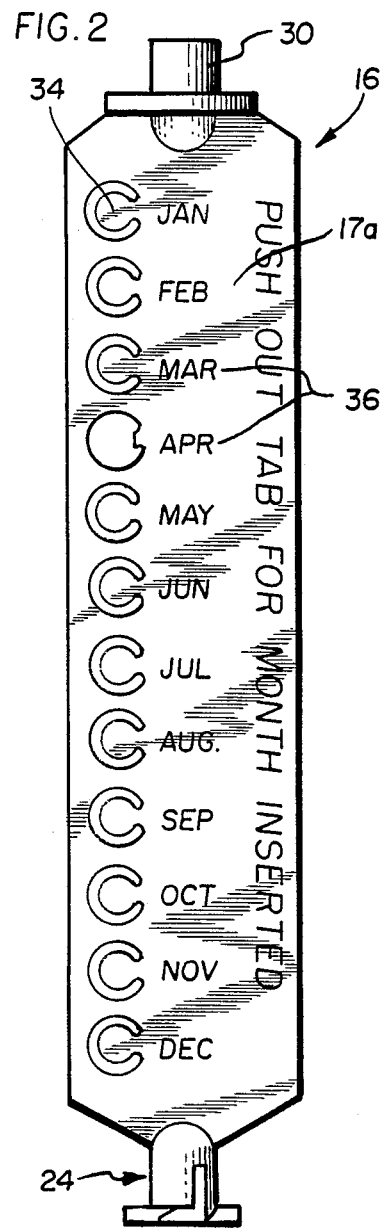

Referring in more detail and by reference characters to the drawings, FIG. 1 illustrates a typical lens disinfection case 10, including a container 12, and a convoluted, catalytic split ring 14 with which the instrument 16, shown in a preferred embodiment in FIG. 2, is employed to insert and remove the ring 14 from the container 12. The container 12 has a generally cylindrical body and an open upper end around which are formed threads for receiving the removal of screw cap 18. The cap 18 can have a venting conduit formed therein (not shown) for release of pressurized oxygen generated by decomposition of hydrogen peroxide promoted by the catalytic ring 14 during the lens disinfection process carried out within the capped container, as more fully described in U.S. Pat. Nos. 4,011,941, and 4,637,919.

The cap 18 has a depending, lens-supporting structure 20 which projects downwardly into the container to immerse and retain a pair of lenses in the disinfection fluid when the cap 18 is mounted on the container 12. The lens-supporting structure 20 includes a pair of lens covers or baskets 22 which pivot on the structure 20 to either enclose and retain the lenses or open for manual access to the lens. When the cap 18 is mounted on the container 12, the lens-supporting structure 20 is suspended above the catalytic ring 14. The ring 14 is removably inserted and retained at the bottom 12a of the container 12 by frictional fit against the interior container wall of three radially-projecting lobes 14a in the illustrated configuration.

Figure 9:
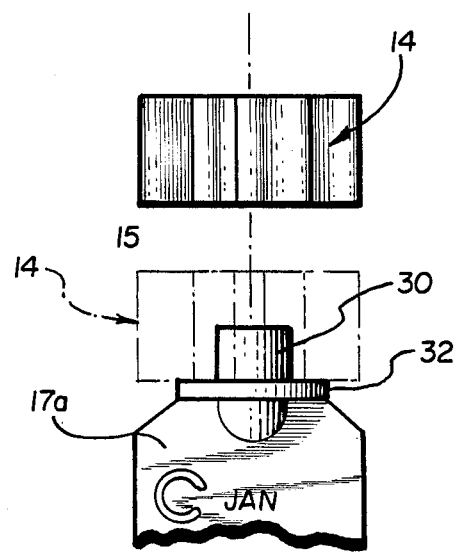
FIG. 9 is an elevation view partially broken away from the upper end of the instrument shown in FIG. 2, and further illustrating mounting of the catalytic ring on the instrument in preparation for insertion of the ring into the lens container.

The instrument 16 is used to remove the frictionally-retained catalytic ring 14 from its position at the bottom of the container 12 from which the ring 14 cannot typically be manually grasped. The instrument 16 can also be employed to insert the catalytic ring 14 into the container 12, which will be later described with reference to FIG. 9.

Figure 4:
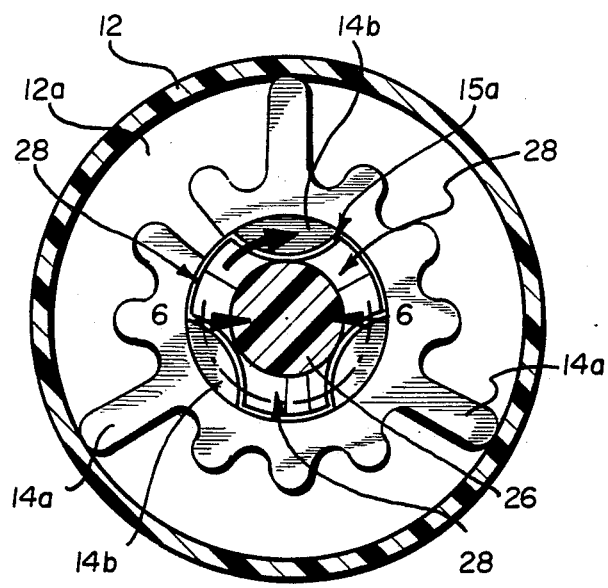
FIG. 4 is a sectional view, viewed from above, illustrating the installed position of the catalytic ring on the bottom wall of the container and insertion of the cam structure through the clearance passageway of the catalytic ring prior to rotation of the cam structure.
Figure 5:
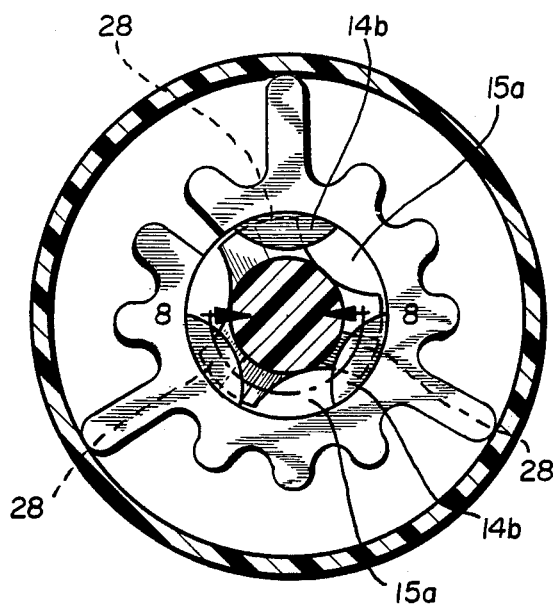
FIG. 5 is a sectional view similar to FIG. 4 illustrating the completed rotation of the cam structure partially underlying the ring which has been lifted from the bottom wall by the camming rotation.

As shown in FIGS. 1 and 4, the catalytic ring 14 has a generally centered and convoluted through passageway 15, and three arcuate spokes 14b which radially project inwardly into the passageway 15 from the wall of the ring 14. As best shown in FIGS. 4 and 5, the spokes 14b are not only radially spaced, but are circumferentially spaced by clearance spaces 15a forming portions of the passageway 15.

Figure 3:
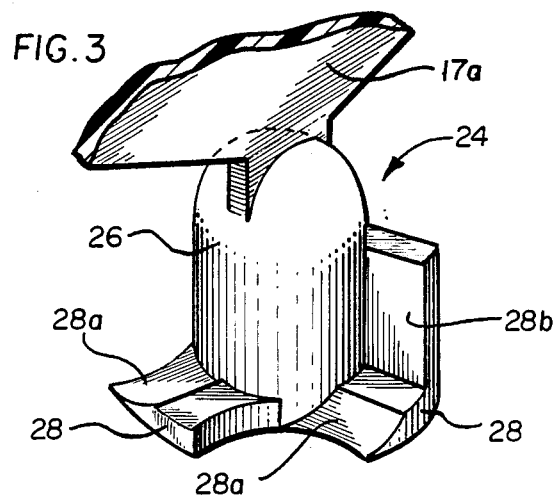
FIG. 3 is an enlarged perspective view broken away from the lower end of FIG. 2 illustrating the ring-removal structure of the instrument.
Figure 6:
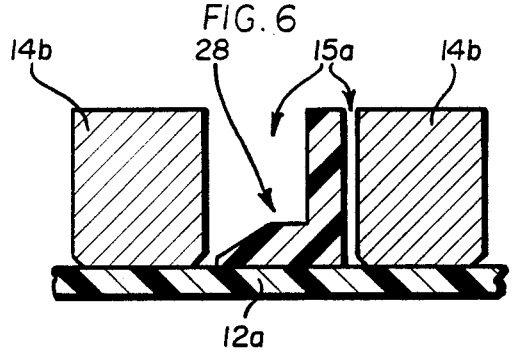
FIG. 6 is a schematic, sectional view taken along line 6—6 in FIG. 4, and illustrating a beveled foot of the cam structure shown in FIGS. 3 and 4.

Referring again to FIGS. 2 and 3, the elongate instrument 16 has a cam structure 24 formed at one end. The cam structure 24 includes a cylindrical stem 26 from which three camming feet 28 (two of which are shown in FIG. 3) radially project outwardly at the terminal periphery of the stem 26. The feet 28 extend generally perpendicular to the cylindrical axis of the stem 26. As shown in FIGS. 4 and 6, the three feet 28 are annularly spaced and dimensioned to fit through the respective clearance spaces 15a of the catalytic ring 14 when the cam structure 24 is lowered into the container 12 and through the passageway 15. Once the feet 28 contact the bottom wall 12a of the container 12, as shown in FIG. 6, the elongate handle portion 17 a can be twisted, for example, approximately 30 degrees as shown in FIG. 5 which will rotate the feet 28 to produce cammed, lifting action of the spokes 14b and ring 14 upon the beveled portions 28a of the respective feet 28. In order to prevent excessive rotation of the feet 28 with respect to the spokes 14b, an axially upstanding stop blade extends upwardly from at least one of the feet 28 to engage a side surface of the respectively-lifted ring spoke 14b as shown in FIG. 8.

After rotating the cam structure 24 to lift the spokes 14b from the container bottom 12a onto the feet 28, the catalytic ring 14 can be upwardly withdrawn by the instrument 16 for removal and replacement by a fresh, catalytically-active ring 14.

Figure 7:
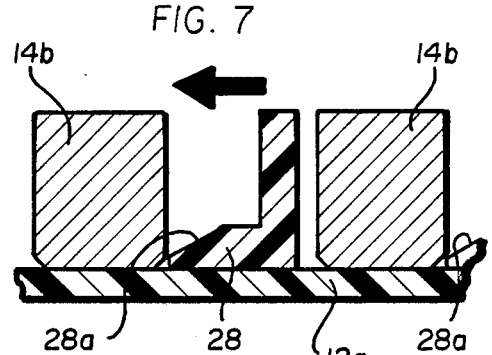
FIG. 7 is a sectional view similar to FIG. 6, illustrating initiation of rotation of the foot engaged against a respective inward projection of the ring.
Figure 8:
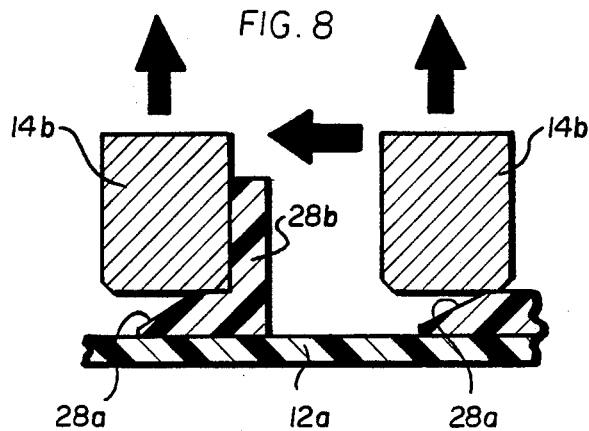
FIG. 8 is a sectional view taken along line 8—8 in FIG. 5 and illustrating the upward displacement of the ring produced by the rotational camming of the feet.

As illustrated in FIGS. 6 to 8, the ring spokes 14b can be chamfered at the lower edges (or even entirely relieved from the remaining bottom surface of the ring) in order to facilitate the smoothly cammed lifting by the beveled feet 28.

Referring again to FIG. 9, to enable insertion of the ring 14 into the container 12, the end of the instrument 16 opposite the cam structure 24 can be formed by a generally cylindrical pin 30 with a diameter dimensioned to project into the catalytic ring passageway 15, preferably in frictional engagement with the ring spoke 14b. Shown in FIG. 4, the catalytic ring 14 can be placed upon a supporting flange 32 formed below the pin 30 which is inserted into the passageway. Thereafter, the inverted container 12 (not shown in FIG. 9) can be lowered over the ring 14 and instrument 16 until the ring reaches the bottom wall of the container where it is frictionally retained and the pin 30 can then be withdrawn from the passageway 15 with retraction of the instrument from the container 12.

Referring again to FIG. 2, the instrument can be provided with an integral memory device for scheduling and reminding the user to remove and replace the ring 14. In the illustrated embodiment, the gripping member 17 is provided with twelve punch-out tabs 34 which are adjacently labeled on the front surface 17a of the gripping member shown in FIG. 2 with respective labels 36 corresponding to calendar months. The tab corresponding to the label of the month in which the ring is removed and replaced can be punched out to record the most recent catalytic ring replacement. Similarly, the opposite surface 17b of the gripping member shown in FIG. 2a can be provided with labels 36 corresponding to months which have a predetermined scheduling stagger, for example three months, so that each tab is provided with two respective labels 36 and 36 indicating both the month of the most recent ring replacement and the month in which the next succeeding replacement should be performed, thus providing a memory device without resort to a calendar separate from the instrument itself. For example, as illustrated in FIG. 2, the punched out tab labeled 36 for April on the front surface 17a is labeled 36 for July on the rear surface 17b shown in FIG. 2a, indicating the next scheduled ring replacement.

While particular embodiments of the invention have been shown and described in detail, it will be obvious to those skilled in the art that changes and modifications of the present invention, in its various aspects, may be made without departing from the invention in its broader aspects, some of which changes and modification being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. An extractor instrument for removing an article having a through passageway and located adjacent the bottom of a container cavity from the open upper end of the container cavity which has an axis generally aligned with said passageway, said instrument comprising an elongate gripping member and a cam structure secured to the gripping member adjacent one end thereof, said cam structure comprising at least one foot extending generally perpendicular to the elongate dimension of said gripping member to enable axial insertion of said foot into said open cavity end, through said article passageway, and engagement of said foot below and against a surface of said article directed away from said open cavity end for subsequent withdrawal of said gripping member and foot to remove the engaged article.

2. The instrument according to claim 1 wherein said foot includes a beveled portion tapering toward a direction of rotation of said gripping member about a central axis of said gripping member aligned parallel to said elongate dimension thereof, in order to enable manual twisting of said gripping member and wedging of said beveled foot portion into said engagement below said article surface for cammed displacement of the article from the bottom of said cavity.

3. The instrument according to claim 1 wherein said foot includes a stop blade formed thereon for engagement with said article to prevent disengagement of said foot prior to removal of the article from said cavity.

4. The instrument according to claim 3 wherein said stop blade extends from said foot in alignment parallel to said elongate dimension of said gripping member.

5. The instrument according to claim 1 wherein said cam structure further comprises a generally cylindrical stem axially parallel to the elongate dimension of said gripping member, wherein said foot extends perpendicularly from the terminal periphery of said stem.

6. The instrument according to claim 5 wherein three of said feet are formed in mutually-spaced arrangement in an annular pattern extending from said stem.

7. The instrument according to claim 1 wherein said gripping member comprises multiple insignia corresponding to a calendar for scheduling and reminding the user to remove said article.

8. The instrument according to claim 7 wherein said insignia comprises twelve tabs removable from said gripping member and respective labels for said tabs corresponding with calendar months.

9. The instrument according to claim 8 wherein said gripping member comprises a generally flat handle on which said months are labeled on both of the opposing surfaces of said handle so that the two labeled months for each said tab are staggered with respect to each other to provide a predetermined sequence for said scheduling.

10. The instrument according to claim 1, further comprising support means located adjacent the end of said gripping member opposite said cam structure, for supporting said article in order to install said article at said container cavity bottom.

11. The instrument according to claim 10 wherein said support means comprises a radially extending flange for axially supporting said article, and a pin axially extending from said flange for insertion through the passageway of said article supported on said flange.

12. A kit for replacement and removal of an article frictionally retained adjacent the bottom of a container cavity from the open upper end of the cavity, comprising in combination a ring having a generally centrally-located through passageway therein and a plurality of annularly-arranged spokes projecting radially inwardly from said ring, said spoke arrangement including alternative clearance spaces between said spokes and defining portions of said passageway; and an extractor instrument comprising an elongate gripping member and a cam structure secured to the gripping member adjacent one end thereof, said cam structure comprising a plurality of feet members extending generally perpendicular to the elongate dimension of said gripping member, said feet members being dimensioned for insertion through said clearance spaces and engagement against a radial surface of said ring for subsequent withdrawal by said gripping member to remove said feet and engaged ring from said cavity bottom.

13. The kit according to claim 12 wherein each said foot includes a beveled portion tapering toward a direction of rotation of said gripping member about a central access aligned parallel to said elongate dimension thereof, in order to enable manual twisting of said gripping member and wedging of said beveled feet portions into said engagement below said respective ring spokes for cammed displacement of the ring from the bottom of said cavity.

14. The kit according to claim 13 wherein at least one of said feet includes a stop blade formed thereon for engagement with said article to prevent disengagement of said foot from said respective spoke prior to removal of the article from said cavity.

15. The instrument according to claim 14 wherein said stop blade extends from said foot in alignment parallel to said elongate dimension of said gripping member.

16. The kit according to claim 12 wherein said gripping member comprises multiple insignia corresponding to a calendar for scheduling and reminding the user to remove said installed article.

17. The kit according to claim 12, wherein said gripping member further comprises a radially extending flange for axially supporting said ring, and a pin axially extending from said flange for insertion through the passageway of said article supported on said flange in order to install said ring at said cavity bottom.

* * * * *